United States Patent [19]

Hertel et al.

[11] Patent Number: 4,888,100
[45] Date of Patent: Dec. 19, 1989

[54] PHOTOCHEMICAL CONVERSION OF CEPHALOSPORINS, 1-CARBA(1-DETHIA)CEPHALOSPORINS AND 1-OXA(1-DETHIA)CEPHALOSPORINS

[75] Inventors: Larry W. Hertel, Indianapolis; John M. Morin, Jr., Brownsburg; Robert T. Vasileff, Indianapolis, all of Ind.

[73] Assignee: Eli Lilly and Company, Indianapolis, Ind.

[21] Appl. No.: 324,169

[22] Filed: Mar. 15, 1989

[51] Int. Cl.$^4$ .............................................. B01J 19/08
[52] U.S. Cl. ............................ 204/157.7; 204/157.71; 204/157.72; 540/205; 540/301; 540/229; 540/215
[58] Field of Search ........... 204/157.7, 157.71, 157.72, 204/157.69

[56] References Cited

PUBLICATIONS

Duhaime et al., *J. Org. Chem.*, 1985, 50, 873–879.
I. A. Skinner and A. C. Weeden, Tetrahedron Letters, 4299, (1983).
M. J. Jorgenson, *Chem. Comm.*, 137–138, 1965.
R. R. Rando and W. von E. Doering, *J. Org. Chem.*, vol. 33, No. 4, Apr. 1968, pp. 1673–1675.
Y. Maki and M. Sako, *J. Am. Chem. Soc.*, 99:15, Jul. 20, 1977, pp. 5091–5096.
Y. Maki and M. Sako, *J. Am. Chem. Soc.*, 97:24, Nov. 26, 1975, pp. 7168–7170.
N. K. Capps et al., *J. Chem. Soc., Chem. Commun.*, 1985, pp. 843–845.

*Primary Examiner*—John F. Niebling
*Assistant Examiner*—Ben C. Hsing
*Attorney, Agent, or Firm*—Bernard J. Graves; Leroy Whitaker

[57] ABSTRACT

A process for photochemically converting 3-exomethylene cephams (or 1-carba(1-dethia)cephams or and 1-oxa(1-dethia)cephams) from the corresponding 3-alkyl-3-cephem (or 1-carba(1-dethia)cephem or 1-oxa(1-dethia)cephem) is provided. Further provided are 3-cephams useful as intermediates to 3-cephem compounds.

19 Claims, No Drawings

PHOTOCHEMICAL CONVERSION OF CEPHALOSPORINS, 1-CARBA(1-DETHIA)CEPHALOSPORINS AND 1-OXA(1-DETHIA)CEPHALOSPORINS

BACKGROUND OF THE INVENTION

This invention belongs generally to the field of β-lactam antibiotics; more particularly, it relates to a process whereby a 3-methyl cephem, 1-carba(1-dethia)cephem, or 1-oxa(1-dethia)cephem is photochemically converted to the corresponding 3-exo-methylene derivative. Such derivatives provide a useful functionality in the 3-position for further derivatization. For example, the 3-exomethylene cepham may be ozonized to provide the 3-(keto)-enol, which, in turn, may be halogenated to form 3-halo cephems [see, for example, S. Kukolja and R. R. Chauvette in "Chemistry and Biology of β-lactam Antibiotics", R. B. Morin and M. Gorman, Eds., Vol. I, Ch. 2, pp. 93–198, Academic Press (1982)].

SUMMARY OF THE INVENTION

The present invention provides a process whereby a 3-methyl cephem, 3-methyl 1-carba(1-dethia)cephem, or 1-oxa(1-dethia)cephem is photochemically converted to the corresponding 3-exomethylene derivative. As an example of the invention, an acetonitrile solution of methyl 7β-acetylamino-3-methyl-3-cephem-4-carboxylate is subjected to ultraviolet radiation of about 2537 Å to provide methyl 7β-acetylamino-3-methenyl-cepham-4-carboxylate.

DETAILED DESCRIPTION

The present invention provides a process for preparing a compound of Formula (I):

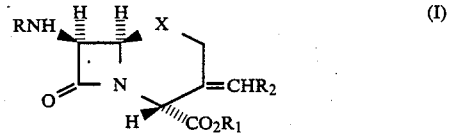

(I)

wherein R is an amino-protecting group, X is —CH$_2$—, O or

wherein n is 0, 1 or 2; R$_1$ is a carboxy-protecting group; and R$_2$ is hydrogen, C$_1$–C$_6$ alkyl, C$_2$–C$_6$ alkenyl, C$_2$–C$_6$ alkynyl, C$_1$–C$_6$ substituted alkyl, C$_2$–C$_6$ substituted alkenyl, C$_2$–C$_6$ substituted alkynyl, C$_1$–C$_6$ alkoxy, C$_1$–C$_6$ alkylthio, C$_2$–C$_6$ alkenyloxy, C$_2$–C$_6$ alkenylthio, C$_2$–C$_6$ alkynyloxy, C$_2$–C$_6$ alkynylthio, C$_1$–C$_6$ substituted alkoxy, C$_1$–C$_6$ substituted alkylthio, C$_2$–C$_6$ substituted alkenyloxy, C$_2$–C$_6$ substituted alkenylthio, C$_2$–C$_6$ substituted alkynyloxy, and C$_2$–C$_6$ substituted alkynylthio; which comprises subjecting a compound of Formula (II)

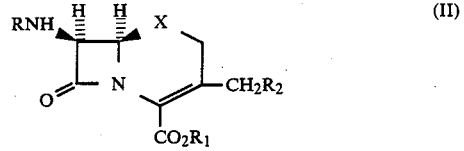

(II)

to ultraviolet radiation, wherein R, R$_1$ and R$_2$ are as defined above.

The term "amino-protecting group" as used in the specification refers to substituents of the amino group commonly employed to block or protect the amino functionality while reacting other functional groups on the compound. Examples of such amino-protecting groups include the formyl group, the trityl group, phenoxyacetyl, benzoyl, substituted benzoyl, such as methylbenzoyl, chlorobenzoyl, nitrobenzoyl, and the like, trimethylsilyl, the acetyl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl, and the like; the benzoylmethylsulfonyl group, the 2-(nitro)phenylsulfenyl group, the diphenylphosphine oxide group, and like amino-protecting groups. The species of amino-protecting group employed is not critical so long as the derivatized amino group is stable to the process herein and can be removed without disrupting the remainder of the molecule. Preferred amino-protecting groups are the allyloxycarbonyl, the acetyl, t-butoxycarbonyl, and the trityl groups. Typical amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, NY, 1973, Chapter 2, and T. W. Greene, "Protective Groups in Organic Synthesis", John Wiley and Sons, New York, NY, 1981, Chapter 7. The related term "protected amino" defines an amino group substituted with an amino-protecting group discussed above.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include methyl, trimethylsilylethyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, $\beta$-(trimethylsilyl)ethyl, $\beta$-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the process herein and can be removed without disrupting the remainder of the molecule. Preferred carboxylic acid protecting groups are the allyl, methyl, and trimethylsilylethyl. Similar carboxy-protecting groups used in the cephalosporin, penicillin and peptide arts can also be used to protect a carboxy group substituent. Further examples of these groups are found in E. Haslam, "Protective Groups in Organic Chemistry", J. G. W. McOmie, Ed., Plenum Press, New York, NY, 1973, Chapter 5, and T. W. Greene, "Protective Groups in Organic Synthesis", John Wiley and Sons, New York, NY, 1981, Chapter 5.

In the above formulae, $C_1$-$C_6$ alkyl refers to straight and branched chain alkyl groups such as methyl, ethyl, n-propyl, isopropyl, n-butyl, t-butyl n-pentyl, n-hexyl, 3-methylpentyl, and like alkyl groups. $C_1$-$C_6$ substituted alkyl refers to the same $C_1$-$C_6$ alkyl residues, further substituted by one or more groups selected from a group consisting of cyano, fluoro, bromo, chloro, iodo, carboxy, nitro, hydroxy, or amino. The terms $C_1$-$C_6$ alkylthio, $C_1$-$C_6$ alkoxy, $C_1$-$C_6$ substituted alkylthio, and $C_1$-$C_6$ substituted alkoxy refer to like $C_1$-$C_6$ alkyl or substituted alkyl groups attached to the substrate via an oxygen or sulfur atom.

As used herein, the term $C_2$-$C_6$ alkenyl refers to straight and branched olefins. Examples of the term $C_2$-$C_6$ alkenyl include ethenyl, 1-propenyl, 2-propene-1-yl, 1-butene-1-yl, 2-butene-1-yl, 3-butene-1-yl, 1-pentene-1-yl, 2-pentene-1-yl, 3-pentene-1-yl, 4-pentene-1-yl, 1-hexene-1-yl, 2-hexene-1-yl, 3-hexene-1-yl, 4-hexene-1-yl, 5-hexene-1-yl, isoproprene-1-yl, isobutenyl, isopentenyl, isohexenyl, and the like. The term $C_2$-$C_6$ substituted alkenyl refers to a $C_2$-$C_6$ alkenyl group substituted by one or more chlor, bromo, iodo, fluoro, hydroxy, nitro, cyano, carboxy, or amino groups.

The terms $C_2$-$C_6$ alkenylthio, $C_2$-$C_6$ alkenyloxy, $C_2$-$C_6$ substituted alkenylthio, and $C_2$-$C_6$ substituted alkenyloxy refer to the same $C_2$-$C_6$ alkenyl or substituted alkenyl groups attached to the substrate via an oxygen or sulfur atom.

As used herein, the term $C_2$-$C_6$ alkynyl refers to straight and branched acetylenic groups. Examples of the term $C_2$-$C_6$ alkynyl include ethynyl, 1-propyne-1-yl, 2-propyne-1-yl, 1-butyne-1-yl, 2-butyne-1-yl, 3-butyne-1-yl, 1-pentyne-1-yl, 2-pentyne-1-yl, 3-pentyne-1-yl, 4-pentyne-1-yl, 1-hexyne-1-yl, 2-hexyne-1-yl, 3-hexyne-1-yl, 4-hexyne-1-yl, 5-hexyne-1-yl, 2-methyl-2-propyne-1-yl, 2-methyl-4 propyne-1-yl, 2-methyl-3-pentyne-1-yl, 2-methyl-3-butyne-1-yl, and the like. The term $C_2$-$C_6$ substituted alkynyl refers to a $C_2$-$C_6$ alkynyl group substituted by one or more chloro, bromo, hydroxy, or nitro. The terms $C_2$-$C_6$ alkynylthio, $C_2$-$C_6$ alkynyloxy, $C_2$-$C_6$ substituted alkynylthio, and $C_2$-$C_6$ substituted alkynyloxy refer to the same $C_2$-$C_6$ alkynyl or substituted alkynyl groups attached to the substrate via an oxygen or sulfur atom.

The process of the invention may be carried out in an inert solvent at a temperature between about 0° C. and about 80° C. Inert solvents are commonly used solvents which do not interfere in the desired reaction.

The choice of solvent is not highly critical, so long as the solvent is of sufficient polarity so as to maintain the substrate of Formula (II) (above) in solution. Such solvents include (but are not limited to) dimethylformamide, $CH_3CN/H_2O$, methanol/$H_2O$, acetic acid, $CH_2Cl_2$, $CH_3CN$, $CH_3CN/CH_3OH$, acetone, tetrahydrofuran, ethyl acetate, and $CHCl_3$.

The time necessary for completion of the reaction is, of course, dependent primarily upon intensity of the UV light source. Typically, the reaction is complete in 0.5 to 24 h.

In the process of the present invention, the light source may be generated from commercially available ultraviolet lamps. In the examples which follow, either a Rayonet® or Hanovia® lamp was utilized. The Rayonet® model RPR-100 2537 Å lamp is advertised to emit primarily 2537 Å light with some emittance of 1849 Å light. While the primary bandwidth emitted from this Rayonet® lamp is 2537 Å there is a considerable amount of ultraviolet radiation of both higher and lower frequency. The Hanovia® lamp emits a much broader spectrum of UV radiation. Further, as one skilled in the art of photochemistry will appreciate, it is often the case that certain filters attached to said UV source will be advisable and at times even necessary to limit the spectrum of UV irradiation to an approximate desired bandwidth. In this regard, preferred filters include the Corex®, Pyrex®, Vycor®, or quartz filters. By using a combination of filters, more narrow desired bandwidths of UV irradiation may be obtained. Further, monochromatic UV light sources of a preferred frequency may be utilized.

It is also sometimes desirable to use an ultraviolet sensitizer such as thiophene, acetic anhydride, 10% acetone, 4-phenylbenzophenone, 2-acetylnaphthalene, hexafluoroacetophenone, benzil, acetophenone, pyrene, benzophenone, or anthracene in the above reaction. It will further be appreciated by one skilled in the art of photochemistry that use of a sensitizer may, in some cases, result in a successful transformation for a given substrate when the same reaction would not occur without said sensitizer when utilizing a given solvent, catalyst, and UV bandwidth combination.

Finally, it is also sometimes desirable to utilize a catalyst such as $NaHCO_3$, acetic acid, triethylamine, DMBA (dimethoxybenzoic acid), dimethyl imidazole, p-toluenesulfonic acid, methylamine, aniline, $NaHCO_3/H_2O$, morpholine, or $NH_4OH$.

The process is carried out in a suitable UV transparent reaction vessel with an external source of UV radiation such as a UV lamp. Alternatively, an immersible UV source such as an immersible UV lamp may be inserted in the reaction solution. The UV source, if desired, is suitably equipped with a filter. The reaction mixture is preferably stirred during irradiation and, as noted above, may contain a sensitizer and a catalyst. The progress of the reaction can be monitored by removing an aliquot of the mixture from time to time and assaying the sample, for example, via high performance liquid chromatography.

The 3-exomethylenecepham ester product (I) is recovered from the reaction mixture by conventional isolation methods. For example, the reaction mixture may be evaporated to dryness and the product mixture chromatographed over silica gel or other material to separate the 3-exomethylenecepham ester. Alternatively, the reaction mixture may be washed with an appropriate acid or base to remove an acidic or basic sensitizer or catalyst from the reaction mixture prior to chromatography.

Examples of amino-protected 3-cephem-4-carboxylic acid esters II which may be employed in the process are t-butyl 7β-(t-butyloxycarbonylamino)-3-methyl-3-cephem-4-carboxylate, benzyl 7β-allyloxycarbonylamino-3-methyl-3-cephem-4-carboxylate, diphenylmethyl 7β-benzyloxycarbonylamino-3-methyl-3-cephem-4-carboxylate 1-oxide, p-methoxybenzyl 7β-(t-butyloxycarbonylamino-3-methyl-1-carba(dethia)-3-cephem-4-carboxylate, 2,2,2-trichloroethyl 7β-propionylamino-3-ethyl-1-oxo(dethia)-3-cephem-4-carboxylate, 2-(trimethylsilyl)ethyl 7β-ethoxycarbonylamino-3-methoxymethyl-3-cephem-4-carboxylate-1,1-dioxide, methyl 7β-acetylamino-3-allyloxymethyl-3-cephem-4-carboxylate, t-butyl, 7β-benzamido-3-ethoxymethyl-3-cephem-4-carboxylate, benzyl 7β-(2,6-dimethoxybenzamido)-3-methyl-3-cephem-4-carboxylate, and like amino-protected and carboxy-protected 3-cephem compounds.

Preferred 3-cephem esters for use in the process are represented by Formula (I) wherein X is sulfur and $R_2$ is hydrogen or $C_1$–$C_6$ alkyl, and the sulfoxide (n=1) and sulfone (n=2) derivatives thereof. Further preferred 3-cephem esters are represented by Formula (II) wherein $R_2$ is hydrogen and R is a substituted benzamido group, especially methyl substituted benzamido.

In a preferred embodiment of the process, methyl 7β-acetylamino-3-methyl-3-cephem-4-carboxylate is dissolved in acetonitrile and a catalytic amount of acetic acid is added to the solution. The solution is irradiated at room temperature for about 1 h with UV radiation (2537 Å) from a Rayonet ® lamp, model RPR-100. The reaction mixture is evaporated to dryness under vacuum and the residue chromatographed over silica gel to provide methyl 7β-acetylamino-3-exomethylenecepham-4-carboxylate.

The 3-exo esters provided by the process (Formula I) are useful as intermediates to known antibiotic compounds. For example, when $R_2$ is hydrogen and X is sulfur, the amino-protecting group is removed to provide the 7-amino-3-exomethylenecepham-4-carboxylic acid ester described by Chauvette, U.S. Pat. No. 3,932,393. This nucleus ester is useful in the preparation of antibiotics such as those described by Chauvette in U.S. Pat. Nos. 3,917,588 and 3,925,372.

As noted above, the process of the present invention is carried out by exposing the substrate to ultraviolet light. Preferably, the ultraviolet light is of a wavelength (λ) of from about 220 nm to about 280 nm. A further preferred bandwidth is from about 240 nm to about 270 nm. An even more highly preferred bandwidth is from about 250 nm to about 265 nm. The most highly preferred ultraviolet radiation is that occurring at about 260 nm.

As a further aspect of the present invention, there is provided compounds of Formula (II)

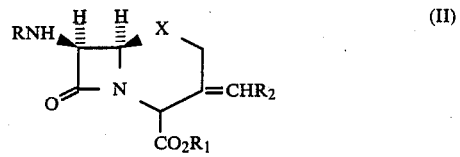

wherein R is an amino-protecting group, X is —$CH_2$—, O, or

wherein n is 0, 1 or 2; $R_1$ is a carboxy-protecting group; and $R_2$ is $C_1$–$C_6$ alkoxy, $C_1$–$C_6$ alkylthio, $C_2$–$C_6$ alkenyloxy, $C_2$–$C_6$ alkenylthio, $C_2$–$C_6$ alkynyloxy, or $C_2$–$C_6$ alkynylthio. Such compounds are useful as intermediates and may be isomerized to the corresponding $\Delta^3$ cephem to provide compounds of Formula (I). Compounds of Formula (I) wherein R is phenoxyacetyl or t-butoxycarbonyl are preferred.

The following Examples are set forth to further illustrate the present invention but are in no manner to be construed as limiting the scope thereof.

EXPERIMENTAL SECTION

EXAMPLE 1

Methyl 7β-acetylamino-3-methenyl-3-cepham-4-carboxylate

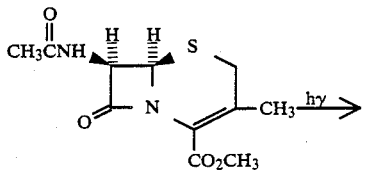

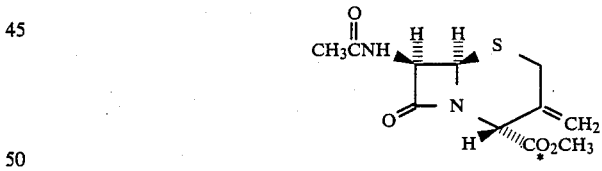

A 27 mg (0.1 millimole) sample of methyl 7β-acetylamino-3-methyl-3-cephem-4-carboxylate was dissolved in 15 ml of $CH_3CN$ and subjected to ultraviolet radiation using a 450-watt Hanovia ® lamp for approximately 1.5 h. High performance liquid chromatography of the reaction mixture indicated an 18% conversion to the title compound. Preparative thin layer chromatography resulted in a small amount (0.5% yield) of the title compound.

*NMR of final product: (300 MHz, $CDCl_3$) δ: 2.0, s; 3.45, q; 3.75, s; 5.1, s; 5.25, d; 5.4, d; 5.65, q; 6.45, d.

Examples 2 to 35 below further illustrate the photochemical conversion of methyl 7β-acetylamino-3-methyl-3-cephem-4-carboxylate to methyl 7β-acetylamino-3-methenyl-3-cephem-4-carboxylate, using a 450-watt Hanovia ® UV lamp:

| Example | Solvent | Filter | Sensitizer | Catalyst | % yld exo HPLC | % yld Chrom |
|---|---|---|---|---|---|---|
| 2 | DMF | Corex | none | NaHCO$_3$ | 7 | 2 hrs |
| 3 | CH$_3$CN—H$_2$O | Corex | none | NaHCO$_3$ | 6 | 2 hrs |
| 4 | MeOH—H$_2$O | Corex | none | NaHCO$_3$ | 3.5 | 2 hrs |
| 5 | HOAc | Cores | none | (HOAc) | 3.3 | 2 hrs |
| 6 | CH$_2$Cl$_2$ | Corex | none | Et$_3$N | 0.3 | 2 hrs |
| 7 | CH$_2$Cl$_2$ | Corex | none | DMBA | 0.5 | 2 hrs |
| 8 | CH$_2$Cl$_2$ | Corex | thiophene | none | 0.4 | 2 hrs |
| 9 | CH$_3$CN | Corex | acetic anhydride | none | 1.5 | 2 hrs |
| 10 | CH$_3$CN | Corex | none | none | 0.6 | 2 hrs |
| 11 | CH$_3$CN—MeOH | Corex | none | none | 0.7 | 2 hrs |
| 12 | CH$_3$CN—MeOH | Corex | none | Dimethyl imidazole | 2.9 | 2 hrs |
| 13 | CH$_2$Cl$_2$ | Corex | none | none | 2.3 | 2 hrs |
| 14 | CH$_2$Cl$_2$—MeOH | Corex | none | none | messy | 2 hrs |
| 15 | CH$_3$CN | Pyrex | none | none | 0.03 | 2 hrs |
| 16 | CH$_3$CN | Pyrex | none | Dimethyl imidazole | 0.1 | 2 hrs |
| 17 | THF | Pyrex | none | none | 0.0 | 2 hrs |
| 18 | THF | Pyrex | none | Dimethyl imidazole | 0.0 | 2 hrs |
| 19 | CH$_2$Cl$_2$ | Pyrex | none | none | 0.0 | 2 hrs |
| 20 | CH$_2$Cl$_2$ | Pyrex | none | Dimethyl imidazole | 0.0 | 2 hrs |
| 21 | CH$_3$CN | Pyrex | none | none | 0.3 | 22 hrs |
| 22 | CH$_3$CN | Pyrex | none | Dimethyl imidazole | 3.3 | 22 hrs |
| 23 | Acetone | Pyrex | none | none | 0.0 | 22 hrs |
| 24 | Acetone | Pyrex | none | Dimethyl imidazole | 0.0 | 22 hrs |
| 25 | EtOAc | Pyrex | none | none | 0.3 | 22 hrs |
| 26 | EtOAc | Pyrex | none | Dimethyl imidazole | 0.0 | 22 hrs |
| 27 | CH$_3$CN | Vycor | none | none | 0.0 | 24 hrs |
| 28 | MeOH | Vycor | none | none | 0.0 | 24 hrs |
| 29 | THF | Vycor | none | none | 0.0 | 24 hrs |
| 30 | CH$_3$NO$_3$ | Vycor | none | none | 0.1 | 24 hrs |
| 31 | (MeO)$_3$P | Vycor | none | none | 0.0 | 24 hrs |
| 32 | CHCl$_3$ | Vycor | none | none | 0.0 | 24 hrs |
| 33 | CH$_3$CN | Vycor | none | Dimethyl imidazole | 0.0 | 24 hrs |
| 34 | CHCl$_3$ | Vycor | none | Dimethyl imidazole | 1.0 | 24 hrs |
| 35 | CH$_3$CN | Vycor | none | p-TsOH | 0.0 | 24 hrs |

Examples 36 to 56 illustrate the same conversion as in Examples 1 to 35, except that a Rayonet ® lamp model RPR-100 2537 Å was used as the light source:

| Example | Solvent | Filter | Sensitizer | Catalyst | % yld exo HPLC | % yld Chrom |
|---|---|---|---|---|---|---|
| 36 | CH$_3$CN | none | none | none | 20.2 | 2 hrs |
| 37 | CH$_3$CN | none | none | Dimethyl imidazole | 2.3 | 2 hrs |
| 38 | CH$_3$CN | none | 10% acetone | none | 17.3 | 2 hrs |
| 39 | CH$_2$Cl$_2$ | none | none | none | 5.5 | 2 hrs |
| 40 | CH$_3$CN | none | none | none | 8.3 | 19 hrs |
| 41 | CH$_3$CN | none | none | Dimethyl imidazole | 1.6 | 19 hrs |
| 42 | CH$_3$CN | none | none | none | 25.6 | 75 min |
| 43 | CH$_3$CN | Corex | none | none | 2.5 | 2 hrs |
| 44 | CH$_3$CN | Pyrex | none | none | 0.0 | 2 hrs |
| 45 | CH$_3$CN | 3500 ang | none | none | 0.0 | 3 hrs |
| 46 | CH$_3$CN | none | none | none | 9.4 | 1 hr |
| 47 | CH$_3$CN | none | none | Dimethyl imidazole | 10.3 | 1 hr |
| 48 | CH$_3$CN | none | 10% acetone | none | 7.3 | 1 hr |
| 49 | CH$_3$CN | none | none | Dimethyl analine | 10.4 | 1 hr |
| 50 | CH$_3$CN | none | none | HOAc | 4.2 | 1 hr |
| 51 | CH$_3$CN | none | none | none | 9.6 | 1 hr |
| 52 | CH$_3$CN | none | none | MeNH$_2$ | 17.8 | 1 hr |
| 53 | CH$_3$CN | none | none | Aniline | 12.8 | 1 hr |
| 54 | CH$_3$CN | none | none | Aq NaHCO$_3$ | 22.3 | 1 hr |
| 55 | CH$_3$CN | none | none | Morpholine | 5.7 | 1 hr |
| 56 | CH$_3$CN | none | none | NH$_4$OH | 13.8 | 1 hr |

EXAMPLE 57

Benzhydryl, 7β-toluamido-3-exomethylene-1-dioxo-3-cepham-4-carboxylate

A 1.0 g (1.89 mmoles) sample of benzhydryl, 7β-toluamido-3-methyl-1,2-dioxo-3-cephem-4-carboxylate was dissolved in about 350 ml of degassed anhydrous diethyl ether:tetrahydrofuran (3:1) and was irradiated for about 1.0 h with a 450 watt Hanovia ® mercury arc lamp through a Pyrex immersion well that was water cooled. The solvent was removed in vacuo and purified by preparative thin layer chromatography on silica gel (ether elution). Yield=120 mg (12%).

NMR: (CDCl$_3$, 90 MHz) δ: 2.33 (s, 3H); 3.62 (bs, 2H); 5.1 (d, 1H, J=5 Hz); 5.24 (5, 1H); 5.38 (s, 1H); 5.53 (s, 1H); 6.2 (dd, 1H, J=5 and 10 Hz); 6.78 (s, 1H); 7.25 (m, 14H).

We claim:

1. A process for preparing a compound of Formula (I)

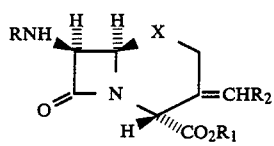
(I)

wherein R is an amino-protecting group, X is —CH$_2$—, O, or

wherein n is 0, 1, or 2, and R$_1$ is a carboxy-protecting group; and R$_2$ is hydrogen, C$_1$–C$_6$ alkyl, C$_2$–C$_6$ alkenyl, C$_2$–C$_6$ alkynyl, C$_1$–C$_6$ substituted alkyl, C$_2$–C$_6$ substituted alkenyl, C$_2$–C$_6$ substituted alkynyl, C$_1$–C$_6$ alkoxy, C$_1$–C$_6$ alkylthio, C$_2$–C$_6$ alkenyloxy, C$_2$–C$_6$ alkenylthio, C$_2$–C$_6$ alkynyloxy, C$_2$–C$_6$ alkynylthio, C$_1$–C$_6$ substituted alkoxy, C$_1$–C$_6$ substituted alkylthio, C$_2$–C$_6$ substituted alkenyloxy, C$_2$–C$_6$ substituted alkenylthio, C$_2$–C$_6$ substituted alkynyloxy, and C$_2$–C$_6$ substituted alkynylthio;

which comprises subjecting a compound of Formula (II)

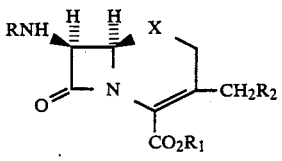
(II)

to ultraviolet radiation, wherein X, R, R$_1$ and R$_2$ are as defined above.

2. The process of claim 1, wherein X is —CH$_2$—.
3. The process of claim 1, wherein X is O.
4. The process of claim 1, wherein X is

5. The process of claim 4, wherein n is 0.
6. The process of claim 4, wherein n is 2.
7. The process of claim 1, wherein the amino-protecting group is chosen from a list consisting of acetyl, phenoxyacetyl, trimethylsilyl, or tert-butyloxycarbonyl.
8. The process of claim 7, wherein the amino-protecting group is acetyl.
9. The process of claim 1, wherein the carboxy-protecting group is methyl, allyl, or trimethyl silyl ethyl.
10. The process of claim 1 wherein R$_2$ is hydrogen.
11. The process of claim 1, wherein the ultraviolet radiation is of the bandwidth from about 220 nm to about 280 nm.
12. The process of claim 11, wherein the ultraviolet radiation is of the bandwidth from about 240 nm to about 270 nm.
13. The process of claim 12, wherein the ultraviolet radiation is of the bandwidth from about 250 nm to about 265 nm.
14. The process of claim 13, wherein the ultraviolet radiation is about 260 nm.
15. The process of claim 11, wherein a catalyst is utilized.
16. The process of claim 15, wherein a catalyst selected from the group consisting of NaHCO$_3$, acetic acid, triethylamine, dimethoxybenzoic acid, dimethyl imidazole, p-toluenesulfonic acid, methylamine, aniline, NaHCO$_3$/H$_2$O, morpholine, or NH$_4$OH is utilized.
17. The process of claim 11, wherein a sensitizer is utilized.
18. The process of claim 17, wherein a sensitizer selected from the group consisting of thiophene, acetic anhydride, 10% acetone, 4-phenylbenzophenone, 2-acetylnaphthalene, hexafluoroacetophenone, benzil, acetophenone, pyrene, benzophenone, or anthracene is utilized.
19. The process of claim 11, wherein a catalyst and a sensitizer are utilized.

* * * * *